(12) United States Patent
McAlister

(10) Patent No.: US 6,402,761 B2
(45) Date of Patent: *Jun. 11, 2002

(54) RETRIEVAL DEVICE MADE OF PRECURSOR ALLOY CABLE

(75) Inventor: Gary B. McAlister, Franklin, MA (US)

(73) Assignee: SciMed Life Systems, Inc., Maple Grove, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/801,186

(22) Filed: Mar. 8, 2001

Related U.S. Application Data

(63) Continuation of application No. 09/427,553, filed on Oct. 27, 1999, now Pat. No. 6,217,589.

(51) Int. Cl.[7] .............................................. A61B 17/22
(52) U.S. Cl. ...................................................... 606/128
(58) Field of Search ................................ 606/127, 128, 606/106–198, 200

(56) References Cited

U.S. PATENT DOCUMENTS

| | | | |
|---|---|---|---|
| 5,057,114 A | 10/1991 | Wittich et al. |
| 5,064,428 A | 11/1991 | Cope et al. |
| 5,067,957 A | 11/1991 | Jervis |
| 5,238,004 A | 8/1993 | Sahatjian et al. |
| 5,330,482 A | 7/1994 | Gibbs et al. |
| 5,601,572 A | 2/1997 | Middleman et al. |
| 5,725,570 A | 3/1998 | Heath |
| 5,868,754 A | 2/1999 | Levine et al. |
| 6,042,553 A | 3/2000 | Solar et al. |
| 6,217,589 B1 | 4/2001 | McAlister |

FOREIGN PATENT DOCUMENTS

| | | |
|---|---|---|
| WO | 91/15152 | 10/1991 |
| WO | 92/22254 | 12/1992 |
| WO | 93/19803 | 10/1993 |
| WO | 98/36694 | 8/1998 |

Primary Examiner—Jeffrey A. Smith
(74) Attorney, Agent, or Firm—Finnegan, Henderson, Farabow, Garrett & Dunner, LLP

(57) ABSTRACT

A medical retrieval device for retrieving foreign objects from a patient, the method of constructing the device, and the method of using the device are disclosed. The device incorporates a wire cable composed of a precursor alloy to a superelastic material to improve durability of the device. Because precursor alloys exhibit a linear stress-strain relationship and a yield point associated with a relatively high stress level, the device transfers greater stresses before experiencing deformation. Thus, greater crushing forces can be achieved using a device of this type. These crushing forces may be needed when the foreign object is too large to remove intact. This property also facilitates the device in dilating ducts to retrieve foreign objects. Using the precursor alloy additionally eliminates the need for heat treatment of the cables used in constructing the device. A retrieval device made of precursor alloy cable also is less susceptible to permanent deformation and unwinding during use.

29 Claims, 2 Drawing Sheets

RETRIEVAL DEVICE MADE OF PRECURSOR ALLOY CABLE

This is a continuation of application Ser. No. 09/427,553, filed Oct. 27, 1999, now U.S. Pat. No. 6,217,518, which is incorporated herein by reference.

FIELD OF THE INVENTION

The present invention pertains to a medical device used to extract foreign objects from a patient. More specifically, the invention relates to an endoscopic device used to retrieve, crush, and remove gallstones and the like. The device is designed to traverse through narrow passages within the body and to open within those passages to retrieve the foreign object.

BACKGROUND OF THE INVENTION

The removal of foreign bodies from patients often requires the use of endoscopic devices. In particular, gastroenterologists commonly use grasping or crushing devices to extract stones from a patient's biliary duct. Additionally, snares are often used when removing stents or other foreign objects.

Grasping and crushing devices generally take the form of wire baskets that deploy to capture the stone to be extracted. These wire baskets may be used for lithotripsy if the stone is too large to be removed intact. Lithotripsy involves crushing the stone into fragments to facilitate removal from the duct. Effective performance of such devices requires the baskets to have enough flexibility to be inserted into the common bile duct. However, the baskets also must have a certain degree of rigidity to dilate the duct to facilitate stone capture. Often, the baskets are deployed using a retaining cannula. In this case, the cannula retains the basket in a retracted configuration during insertion into the bile duct. Once within the grasping region of a stone, the basket extends from the cannula and opens to capture the stone. In such a case, the basket must have enough stiffness to open the duct when removed from the cannula, without being so stiff that it is permanently deformed due to retention within the cannula.

Aside from deformation associated with dilating the duct or retention within the cannula, a common failure of conventional baskets occurs during lithotripsy when the baskets are subject to forces often in excess of 50 pounds. Under such force, the basket can become severely deformed, rendering it unsuitable for repeated use. Such repeated use is desirable because of the frequent occurrence of the need to remove more than one stone or other object at a time from the patient. Therefore, design of these devices includes focus on the durability of the basket in repeated use settings.

To repeatedly crush and retrieve foreign objects, a basket must be flexible enough to traverse tortuous anatomy, yet stiff enough to open within a duct, and strong enough to crush stones. A single wire construction may meet any one of these criteria, but typically cannot meet all three requirements for repeated dilation and lithotripsy. It has been proposed, therefore, to construct a retrieval basket of a stranded cable, such as stainless steel cable. Purely stainless steel cable (the core and strands) may work well for the extraction of a single stone, but is subject to the deformation problems discussed previously when used for repeated dilatation or lithotripsy.

Other baskets are formed from cable which includes a superelastic, sometimes referred to as shape memory, core wrapped with strands of stainless steel to surround the core. Nitinol is often used as the superelastic core in these devices. Nitinol is a specially heat-treated Titanium-Nickel (Ti—Ni) alloy, preferably approximately 55%/45% Nickel to Titanium (Ni—Ti). These baskets require heat treatment for the core to retain its shape. Such a configuration allows for some improvement in performance when the baskets are used repeatedly and for lithotripsy because the superelastic core better retains its shape.

However, superelastic materials of this type experience phase transformations when subject to a certain level of stress loading. Lithotripsy often reaches these stress levels. Upon a phase transformation, the core of the cable stretches, rendering the device incapable of transferring force to the stone to complete the crushing process. Furthermore, the superelastic alloy has a greater reversible elongation than do the surrounding stainless steel strands. This results in a difference in deformation between the core and the surrounding strands leading to a permanent deformation of the cable. Such deformation results in an alteration of the basket shape, making it less desirable to use for its intended purpose.

Moreover, manufacturing both the cable core and strands from superelastic alloy wires results in a cable that unwinds due to the highly elastic nature of the material. Thus, a retrieval basket of such cable also will not retain its desired shape without heat treating.

SUMMARY OF THE INVENTION

The advantages and purpose of the invention will be set forth in part in the description which follows, and in part will be obvious from the description, or may be learned by practice of the invention. The advantages and purpose of the invention will be realized and attained by means of the elements and combinations particularly pointed out in the appended claims.

To attain the advantages and in accordance with the purpose of the invention, as embodied and broadly described herein, the invention includes a medical retrieval device for retrieving foreign objects from within a patient's body. The retrieval device includes a retrieval assembly containing a cable preformed into a configuration for capturing and removing the foreign object. The retrieval cable includes wire made of a precursor alloy to a superelastic material. According to a particularly preferred embodiment of the invention, the cable includes a core wire and surrounding wire strands, each made of the precursor alloy.

The invention further includes a method of manufacturing the medical retrieval device including the steps of constructing a cable including a wire made of a precursor alloy to a superelastic material and forming a retrieval assembly by preforming the cable into a configuration adapted to capture and remove the foreign objects.

The precursor alloy according to the present invention exhibits a stress-strain curve having a linear relationship extending through a yield point with no phase transformation point. After the yield point, the stress-strain curve does not exhibit a substantially constant stress plateau as strain increases. Rather, the precursor alloy exhibits plastic deformation properties.

It is to be understood that both the foregoing general description and the following detailed description are exemplary and explanatory only and are not restrictive of the invention, as claimed.

BRIEF DESCRIPTION OF THE DRAWINGS

The accompanying drawings, which are incorporated in and constitute a part of this specification, illustrate the preferred embodiments of the invention and, together with the description, serve to explain the principles of the invention. In the drawings.

DESCRIPTION OF THE PREFERRED EMBODIMENTS

The various aspects of this invention generally pertain to a device, and a method for manufacturing such a device, for retrieving foreign objects in a body from locations requiring traversal of narrow passages. In use, such a device must be able to collapse into a relatively narrow space for traversal purposes and to expand in that space for retrieval purposes. The device also must have strength characteristics so that the device can crush objects to facilitate capturing and removal. Additionally, the device must reconfigure to its original shape when expanded and retain its ability to reconfigure to the original shape for repeated deployments without losing strength and without suffering permanent deformation.

To accomplish these objectives and to overcome the problems associated with existing devices of this kind, a retrieval device of the present invention incorporates a precursor alloy into the stranded cable used for making the device. When subject to heat treatment, a precursor alloy results in the formation of a superelastic alloy. Prior to heat treatment, such a precursor alloy exhibits high elongation and a linear stress-strain relationship with a yield point. Because of these properties, the use of a precursor alloy in the manufacture of the device according to the present invention achieves greater strength, longer life, and ease in manufacture, as will be explained.

Figure 1A:
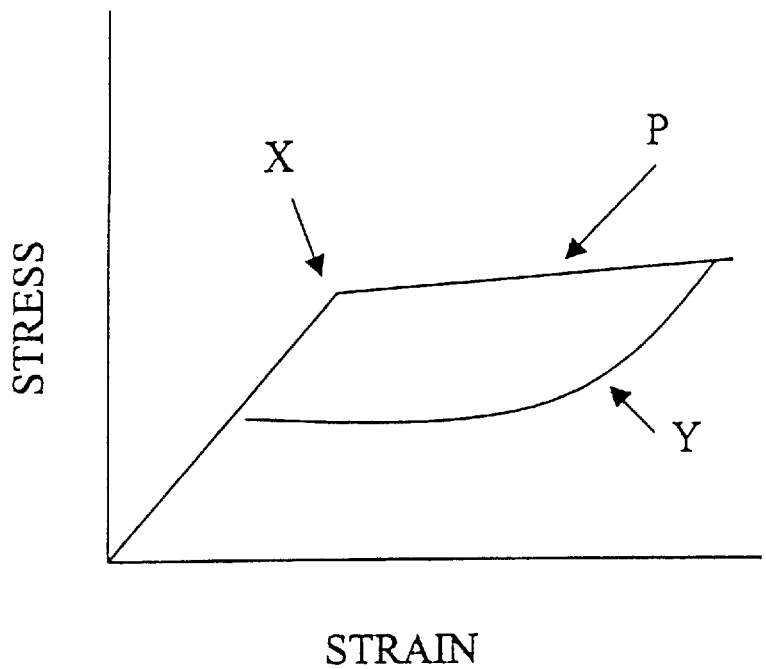
FIG. 1a is a stress-strain curve for a superelastic alloy.
Figure 1B:
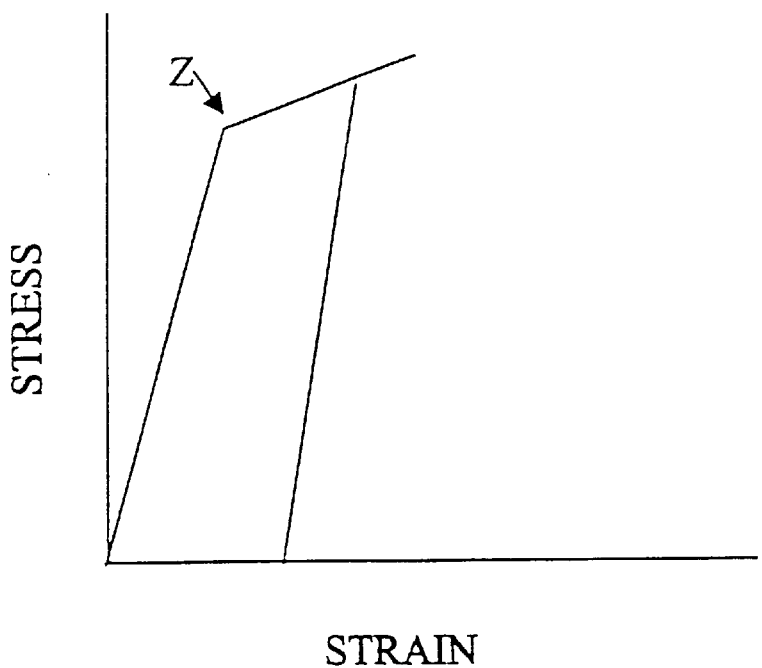
FIG. 1b is a stress-strain curve for a precursor alloy.

Unlike a superelastic alloy, a precursor alloy used in a medical retrieval device of the present invention exhibits a linear stress-strain relationship with a plastic yield point. For comparison purposes, schematics of the stress-strain curves for a superelastic alloy and a precursor alloy are shown in FIGS. 1a and 1b, respectively. As shown in FIG. 1a, as a superelastic alloy undergoes increased stress, strain increases to phase transformation point X. At X, the superelastic alloy transforms from an austenitic phase to a martensitic phase. Thereafter, stress remains substantially constant as strain increases, forming a substantially constant stress plateau P. Upon releasing the stress on the superelastic alloy, the reversibly deformable nature of the material allows it to return to its original length following curve Y in the Figure. The cycle shown often occurs repeatedly with no appreciable change in dimension or plastic deformation of the wire. Therefore, the superelastic alloy withstands a relatively large strain prior to the phase transformation point, and additional strain during the phase transformation, without plastic deformation. Furthermore, the phase transformation and reversible deformation of the superelastic alloy occurs at relatively low stress levels. During the superelastic alloy phase transformation, applied stress is absorbed by the alloy to facilitate the phase transformation, and is not available to be transferred to another object, such as a stone.

A precursor alloy material exhibits the stress-strain characteristics shown in FIG. 1b. Up to the plastic yield point Z, strain increases in a reversible manner as stress increases. That is, the precursor alloy returns to its normal configuration upon release of stresses prior to reaching plastic yield point Z. Moreover, the precursor alloy does not pass through a substantially constant stress plateau as does the superelastic alloy. At stresses above yield point Z, the precursor alloy becomes plastically and irreversibly deformed, unlike the superelastic alloy. As shown in FIGS. 1a and 1b, yield point Z of the precursor alloy generally occurs at higher stress levels than does phase transformation point X of the superelastic material. This enables the device of the present invention to transfer greater stress to stones during lithotripsy, as well as facilitating dilation of ducts. Accordingly, the inventive devices facilitate retrieval and removal, while maintaining shape and strength over repeated uses.

In addition to requiring heat treatment of the precursor alloy to produce the superelastic material, a conventional retrieval device also requires heat treatment during the formation of the basket so that the superelastic wires maintain their shape. In contrast, a result of the plastic yield point associated with a precursor alloy, the basket of the present device forms easily by mechanically bending the precursor alloy wire beyond its yield point and into shape. Sophisticated heat treatments are thus unnecessary in the manufacture of the inventive device.

Moreover, because of the superelastic nature of the heat-treated alloys used in conventional devices, a stranded cable made entirely of a superelastic material is ineffective due to phase transformation deformation and unwinding problems, as mentioned above. However, precursor alloys are highly elastic but also can be plastically deformed. Thus, in a preferred embodiment of the present invention, a cable for a retrieval device is made entirely of a precursor alloy core and precursor alloy strands. It is contemplated that the strands and the core can be made of identical precursor alloy or different precursor alloys. If different precursor alloys are used, it is preferred to select wire dimensions and types such that the wires exhibit similar deformations when subjected to a given load. In either case, the cable will experience neither unwinding nor excessive deformation as would a cable that includes superelastic strands. Furthermore, using a consistent material configuration for both the strands and the core would eliminate problems associated with elongation of the core relative to the surrounding strands leading to permanent damage to the basket. Finally, a cable made entirely of wires of the same precursor alloy material facilitates the manufacturing process.

Figures 2A, 2B:
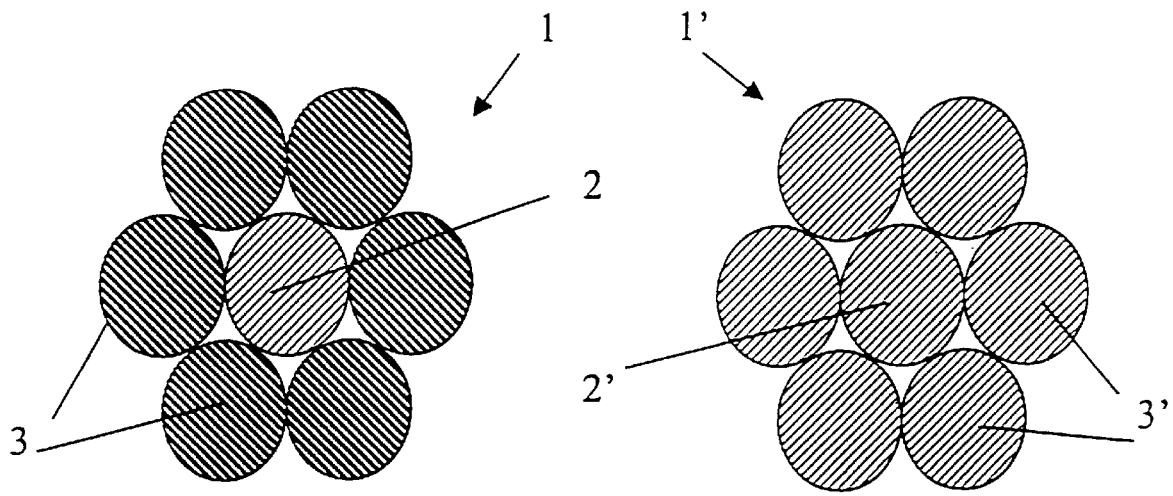
FIG. 2a is a cross-sectional view of one embodiment of a stranding configuration according to the present invention, wherein a core of precursor alloy is surrounded by strands of stainless steel wires.
FIG. 2b is a cross-sectional view of another embodiment of a stranding configuration according to the present invention, wherein a core of precursor alloy is surrounded by strands of precursor alloy wire.
Figure 3:
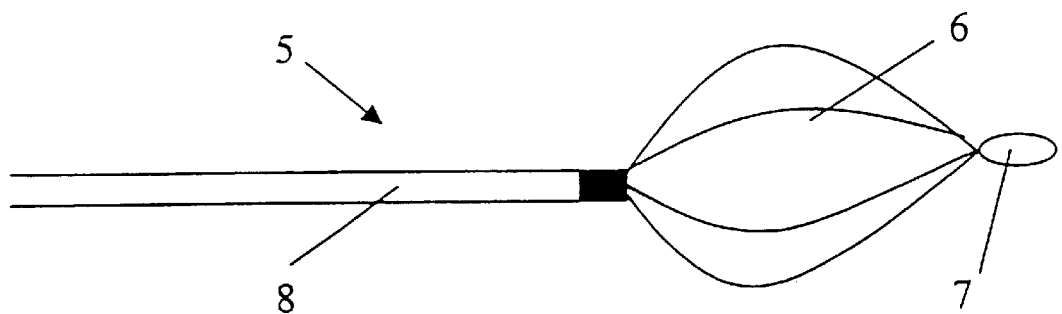
FIG. 3 is a wire basket retrieval device according to an embodiment of the present invention and in a deployed position for retrieving an object.

Reference will now be made in detail to the present exemplary embodiments of the invention, examples of which are illustrated in FIGS. 2 and 3. Wherever possible, the same reference numbers will be used throughout the drawings to refer to the same or like parts.

In accordance with embodiments of the present invention, an endoscopic retrieval device 5 is formed from a stranded cable having the basic configuration shown in either FIG. 2a or FIG. 2b. FIG. 2a shows a cross-section of cable of a first embodiment of the device 5. A cable 1 includes a core monofilament wire 2 made of precursor alloy. Surrounding core wire 2 are strands 3 of stainless steel wire. Due to the presence of the precursor alloy core wire 2, device 5 suffers from less deformation problems than does a conventional device of this type that includes a superelastic core. This is because, as previously discussed, precursor alloys exhibit less elongation than do superelastic materials and therefore differences in the elongation between surrounding strands 3 and core wire 2 will be minimized.

FIG. 2b shows a more preferred embodiment of a stranded cable for use in the endoscopic retrieval device 5. In this embodiment, a cable 1' includes a core wire 2' made of a precursor alloy, as in FIG. 2a. However, surrounding strands 3' in this embodiment also are formed of precursor alloy, either of identical or different precursor alloy material as core wire 2'. As discussed previously, this embodiment is preferred because the cables made entirely of precursor alloy wires (core and strands) will not unwind and are capable of transferring greater stress to objects without deforming. Additionally, cables made of entirely of the same precursor alloy alleviate deformation problems associated with different rates of elongation between the core and strands. When selecting wires of different precursor alloys, it is preferable to impart consistent mechanical properties to the It cable. A person having ordinary skill in the art would realize that such consistency can be achieved by varying such factors as, for example, the nature of the alloys of the surrounding strands and core wire, relative dimensions of the core wire and the surrounding strands, the winding pattern of the strands around the core wire, and the post processing of the cable.

FIGS. 2a and 2b show six surrounding wire strands 3 and 3', respectively. Preferably, there are at least five surrounding wire strands 3 or 3'. However, it is contemplated that the number of surrounding strands can be varied in accordance with the particular use for the device or the desired characteristics of the cable.

In both FIGS. 2a and 2b, the precursor alloy is in a martensitic phase at room temperature to body temperature. The precursor alloy can be a precursor Nitinol or other material exhibiting like properties and known to those having ordinary skill in the art. Such other precursor alloys that may be used include, for example, Silver-Cadmium, Gold-Cadmium, Gold-Copper-Zinc, Copper-Zinc, Copper-Zinc-Aluminum, Copper-Zinc-Tin, Copper-Zinc-Xenon, Iron-Beryllium, Iron-Platinum, Indium-Thallium, Iron-Manganese, Nickel-Titanium-Vanadium, Iron-Nickel-Titanium-Cobalt, and Copper-Tin.

In one preferred form of the invention, the overall diameter of the cable is approximately 0.017 inches. The materials used for the precursor alloy, the number of strands forming the cable, and the overall diameter of the cable can be modified according to the particular use or desired characteristics of the device. The selection of these parameters would be obvious to one having ordinary skill in the art.

FIG. 3 shows the overall construction of endoscopic retrieval device 5. Typically, four cables 1 or 1'form basket 6. However, any number of cables can be used and would be obvious to one having ordinary skill in the art depending on the use or desired characteristics of the basket. A bullet-shaped nosepiece 7 can be attached to a distal end of device 5 to improve guidance of device 5 during use, as well as to secure cables 1 or 1' to each other. A coupling tube 8, attached to a proximal end of basket 6, also facilitates manipulation of device 5 during the retrieval process. Coupling tube 8 also could take the form of a cannula, in which case basket 6 would retract into the cannula prior to retrieval. is. Laser welding represents one preferred mode of attachment of bulletshaped nosepiece 7 and coupling tube 8 to basket 6. However, other suitable attachment methods known to those skilled in the art are within the scope of the present invention. Device 5 is used to traverse narrow passages to retrieve, crush, and remove foreign objects within the body. Device 5 can be deployed from a cannula or traverse independently through the body, collapsing and deploying as necessary. Device 5 also may be used repeatedly to retrieve, crush, and remove foreign objects.

The manufacture of device 5 first involves forming cables 1, 1'. To form these cables, a precursor alloy wire is supplied as the core wire and surrounding strands of wire are placed approximately evenly-spaced around the perimeter of the core wire. Surrounding strands wrap around the core in an essentially helical fashion along its length. The strands can be wrapped clockwise, counterclockwise, or any combination thereof, depending on the desired properties of the cable. A preferred embodiment has strands wrapping clockwise around the core wire, similar to threads of a right-hand screw. The cable can then be rotary swaged, which helps to straighten it and increase its column strength. As discussed with reference to FIGS. 2a and 2b, the surrounding strands can be made of stainless steel, or other like, suitable material, or most preferably precursor alloy.

Several cables, preferably approximately four cables 1 or 1', are then bent past the yield point of either the precursor alloy or stainless steel to form basket 6. After forming basket 6, cables 1 or 1' are joined together at one end, through welding or other suitable joining method known to those skilled in the art. Laser welding cables 1 or 1' to coupling tube 8 or, if desired, to the retractable portion of a retaining cannula, represents another method to connect and secure the cables to each other. As discussed with reference to FIG. 3, a nosepiece can be laser welded, or otherwise attached in any suitable manner, to the end of basket 6 to guide device 5 through the body. It is important that during welding or other connecting operations involving heat, that temperature is controlled to prevent heat treating the cable such that the precursor alloys are converted to superelastic materials.

The stranded cable configuration used in the retrieval device according to the present invention provides the durability necessary to perform lithotripsy and dilation and be repeatedly employed for retrieval processes. Incorporating precursor alloy wire into the cable as opposed to a superelastic material such as Nitinol enables the device to be manufactured without heat treatment processes. Additionally, because precursor alloys do not exhibit the extreme elongation characteristic of superelastic materials, problems of permanent deformation are alleviated when surrounding stainless steel wire strands are used to form the cable. Using precursor alloys also allows for the manufacture of a cable comprised entirely of precursor alloy wire, including the surrounding strands and the core. Whether identical precursor alloy is used for both, or the precursor alloy used for the strands differs from that used for the core, the device will be capable of transferring greater stress to objects without deformation and will not unwind. Additionally, using the same precursor alloy for both the strands and the core facilitates overall manufacture of the device and provides a device of consistent characteristics that will not deform due to disparate elongation properties within the cables.

Although the use of a basket type retrieval device has been discussed and shown in the Figures, it is contemplated that the device can be of the snare type. A snare made of the precursor alloys discussed above would retain its shape better than conventional stainless steel snare devices. Furthermore, although most of the above discussion pertains to using the inventive device to remove gallstones, it should be appreciated that the devices can be used for removing a variety of other foreign objects having various locations within the body.

It will be apparent to those skilled in the art from consideration of the specification and practice of the invention disclosed herein that various modifications and variations can be made in the endoscopic retrieval device formed of precursor alloy cable of the present invention. Therefore, the invention in its broader aspects is not limited to the specific details and illustrative examples shown and described in the specification. It is intended that departures may be made from such details without departing from the true spirit or scope of the general inventive concept as defined by the following claims and their equivalents.

What is claimed is:

1. A method for retrieving foreign objects from a patient's body, the method comprising:
    providing a retrieval device including a cable preformed into a basket-like configuration, said cable including a core wire made of precursor alloy to a superelastic material and a plurality of wire strands surrounding the core wire;
    inserting the retrieval device into a patient's body at a site of a foreign object; and
    capturing, crushing, and removing the foreign object with the retrieval device.

2. The method of claim 1, further comprising the steps of capturing, crushing, and removing a second foreign object with the retrieval device.

3. The method of claim 2, wherein inserting the retrieval device includes inserting the retrieval device into a lumen of the patient's body.

4. The method of claim 1, further comprising dilating a duct in the patient's body during retrieval of the foreign object.

5. The method of claim 1, wherein the capturing, crushing, and removing the foreign object occurs without substantial permanent deformation to the retrieval assembly.

6. The method of claim 5, wherein the capturing, crushing, and removing the foreign object includes applying a force of at least 50 pounds to the retrieval assembly.

7. The method of claim 1, wherein the capturing, crushing, and removing the foreign object occurs without substantially unwinding the cable.

8. The method of claim 1, wherein inserting the retrieval device includes inserting the retrieval device endoscopically.

9. The method of claim 1, wherein said precursor alloy exhibits a stress-strain curve that is linear extending to a yield point.

10. The method of claim 9, wherein said stress-strain curve has no phase transformation point.

11. The method of claim 9, wherein said stress-strain curve extends to a yield point without passing through a substantially constant stress plateau while strain is varied.

12. The method of claim 1, wherein the plurality of wire strands includes five wire strands.

13. The method of claim 1, wherein said plurality of wire strands includes strands made of stainless steel.

14. The method of claim 1, wherein said plurality of wire strands includes strands made of the precursor alloy.

15. The method of claim 1, further comprising retaining the retrieval assembly in a retaining cannula during the inserting of the retrieval assembly.

16. The method of claim 15, further comprising removing the retaining cannula from at least a distal end of the retrieval assembly after the inserting.

17. A method for retrieving foreign objects from a patient's body, the method comprising:
    inserting an endoscopic retrieval device into a patient's body to a site of a foreign object, the retrieval device including a cable including a core wire made of precursor alloy to a superelastic material and a plurality of wire strands surrounding the core wire;
    expanding the retrieval device from a collapsed configuration to an expanded configuration; and
    capturing, crushing, and removing the foreign object from the patient's body with the retrieval device.

18. The method of claim 17, wherein expanding the retrieval device includes dilating a duct of the patient in which the retrieval device is inserted.

19. The method of claim 17, wherein inserting the retrieval device includes inserting the retrieval device in a collapsed configuration within a retaining cannula.

20. The method of claim 19, wherein expanding the retrieval device includes removing the retaining cannula from at least a portion of the retrieval device.

21. The method of claim 17, further comprising the steps of capturing, crushing, and removing a second foreign object with the retrieval device.

22. The method of claim 17, wherein the capturing, crushing, and removing the foreign object occurs without substantial permanent deformation to the retrieval assembly.

23. The method of claim 17, wherein the capturing, crushing, and removing the foreign object includes applying a force of at least 50 pounds to the retrieval assembly.

24. The method of claim 17 wherein the capturing, crushing, and removing the foreign object occurs without substantially unwinding the cable.

25. The method of claim 17, Wherein the cable is preformed into a basket-like configuration.

26. The method of claim 17, wherein the precursor alloy used for each of the core wire and the surrounding wire strands has a plastic yield point.

27. The method of claim 17, wherein said precursor alloy exhibits a stress-strain curve that is linear extending to a yield point.

28. The method of claim 27, wherein said stress-strain curve has no phase transformation point.

29. The method of claim 27, wherein said stress-strain curve extends to a yield point without passing through a substantially constant stress plateau while strain is varied.

* * * * *

UNITED STATES PATENT AND TRADEMARK OFFICE
CERTIFICATE OF CORRECTION

PATENT NO. : 6,402,761 B2  Page 1 of 1
DATED : June 11, 2002
INVENTOR(S) : Gary B. McAlister et al.

It is certified that error appears in the above-identified patent and that said Letters Patent is hereby corrected as shown below:

<u>Column 8,</u>
Line 41, after "claim 17" insert -- , --;
Line 44, replace "Wherein" with -- wherein --.

Signed and Sealed this

Twenty-seventh Day of August, 2002

Attest:

Attesting Officer

JAMES E. ROGAN
Director of the United States Patent and Trademark Office